United States Patent [19]

Hilditch et al.

[11] 4,374,852

[45] Feb. 22, 1983

[54] ANTI-FUNGAL COMPOSITIONS EMPLOYING METAL SALTS OF CARBOXYLIC ACIDS

[75] Inventors: Edward A. Hilditch, Frome; Robert E. Hambling, Warminster; Colin R. Sparks; David A. Walker, both of Frome, all of England

[73] Assignee: Cuprinol Limited, Somerset, England

[21] Appl. No.: 202,216

[22] Filed: Oct. 30, 1980

Related U.S. Application Data

[63] Continuation of Ser. No. 36,271, May 4, 1979, abandoned.

[30] Foreign Application Priority Data

May 5, 1978 [GB] United Kingdom ............... 18026/78

[51] Int. Cl.³ ........................................... A01N 55/02
[52] U.S. Cl. .................................... 424/289; 424/294
[58] Field of Search ................................ 424/289, 294

[56] References Cited

U.S. PATENT DOCUMENTS 2,951,789 9/1960 McCants .............................. 424/289
3,272,693 9/1966 Harrison .............................. 424/294
4,001,400 1/1977 Hager .................................. 424/294

Primary Examiner—Allen J. Robinson
Attorney, Agent, or Firm—Sprung, Horn, Kramer & Woods

[57] ABSTRACT

A mixture of zinc or copper salts of primary and/or secondary saturated acyclic carboxylic acids with zinc or copper salts of a tertiary saturated acyclic carboxylic acid has been found to be of value as a preservative for wood or many other similar degradable organic materials. The mixture can be prepared simply by mixing the salts or by reacting zinc or copper or a suitable zinc or copper compound with a mixture of the appropriate acids.

2 Claims, No Drawings

ANTI-FUNGAL COMPOSITIONS EMPLOYING METAL SALTS OF CARBOXYLIC ACIDS

This is a continuation of application Ser. No. 36,271, filed May 4, 1979, now abandoned.

BACKGROUND TO THE INVENTION

The invention relates to an anti-fungal composition comprising zinc or copper salts of organic acids.

Zinc and copper salts of high molecular weight organic acids have long been used to prevent biological degradation of wood and of other organic materials. Organic acids used to prepare such salts include: those mixtures of acids known as naphthenic acids; tall oil acids; stearic acid; oleic acid; acids derived from linseed oil; and, more recently, mixtures of primary and secondary or tertiary branched-chain carboxylic acids synthesized by various routes from petroleum. For application as a wood preservative, the copper or zinc salt of such an acid is most commonly dissolved in a petroleum solvent (such as paraffin or white spirit) or a coal tar solvent, although it may be dissolved in water by, for example, the technique disclosed in co-pending U.S. patent application No. 904,606, filed May 10, 1978 by Edward Austin Hilditch, now U.S. Pat. No. 4,193,993. For application to organic materials other than wood (for example, hessian, cotton and other textiles, rope and cordage) these salts may be dissolved in the same way as when applied to wood or they may be formed into an emulsion.

However, whatever means is adopted to apply the salts to the material to be treated, once the salts have been applied, it is essential that they should not easily be removed in the course of normal use of the material to which they have been applied.

We have now surprisingly found that the use of a mixture of zinc or copper salts of primary and/or secondary saturated acyclic carboxylic acids with zinc or copper salts of tertiary saturated acyclic carboxylic acids provides a preservative of greater effectiveness than if either type of acid were used alone.

BRIEF SUMMARY OF INVENTION

It is therefore an object of the invention to provide an anti-fungal composition comprising zinc or copper salts having enhanced preservative activity.

It is a further object of the invention to provide a method of preserving wood and other organic materials from fungal attack by the use of a composition comprising the zinc or copper salts.

The present invention provides a mixture of salts of:

(a) a primary and/or a secondary saturated acyclic carboxylic acid; and (b) a tertiary saturated acyclic carboxylic acid with zinc or copper.

The composition of the invention may be a mere mixture of the simple salts or it may comprise a mixed salt of a primary and a secondary saturated acyclic carboxylic acid with a salt of a tertiary saturated acyclic carboxylic acid or it may comprise a mixed salt of a primary or secondary saturated acyclic carboxylic acid with a tertiary saturated acyclic carboxylic acid. The precise nature of the composition will depend upon the method whereby it is prepared.

DETAILED DESCRIPTION OF INVENTION

The mixture of zinc or copper salts (or "soaps") may be prepared by any method known for preparing this type of compound. For example, the salts may be prepared by direct fusion between a suitable zinc or copper compound and the appropriate mixture of acids or by reacting the mixture of acids with an aqueous solution of sodium or potassium hydroxide to form the sodium or potassium salt of the acids and then adding an aqueous solution of a water-soluble zinc or copper salt to precipitate the zinc or copper salt of the organic acids. A variety of zinc and copper compounds can be used for the direct (or "fusion") reaction, for example zinc or copper metal or the oxides, hydroxides, carbonates or acetates of zinc or copper. A variety of water-soluble zinc and copper salts is also available for the double decomposition reaction and examples include the acetates, sulphates, nitrates, chlorides and bromides. Preparation of the salts by any of the methods described above would normally produce a mixture of simple salts of the metal with a single acid and double salts of the metal with two of the acids in the mixture.

Although we prefer that the metal salts are prepared, as described above, from a mixture of the acids, the individual salts may be prepared in a similar manner and the salts then mixed.

The molar ratio of zinc to acid may be the stoichiometric ratio of 1 mole of zinc per 2 equivalents of acid (i.e., where the acid is, as is preferred, monobasic, per 2 moles of acid). Alternatively, more than 1 mole of zinc per 2 equivalents of acid may be used, for example 1.3 or 1.5 moles of zinc. For copper salts, the molar ratio of copper to acid is preferably stoichiometric.

For reasons of commercial availability, the primary and/or secondary saturated acyclic carboxylic acid [component (a) of the composition] is preferably a mixture of isomeric and homologous primary and secondary saturated acyclic carboxylic acids, a major proportion of which contains branched chains. Preferred primary acids have the formula $R.CH_2.COOH$ and preferred secondary acids have the formula

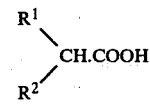

(in which R, $R^1$ and $R^2$ each represents an alkyl group, for example, a methyl, ethyl, n-propyl, isopropyl, n-butyl, isobutyl, sec-butyl, t-butyl, n-pentyl, isopentyl or neopentyl group; $R^1$ and $R^2$ may be the same or different).

In order for the zinc or copper salts to have the desired water-insolubility, oil-solubility and other useful properties for wood preservation, the acid preferably contains from 6 to 20, more preferably from 8 to 13, carbon atoms. Accordingly, R preferably represents an alkyl group containing from 4 to 18 carbon atoms and $R^1$ and $R^2$, which may be the same or different, preferably represent alkyl groups containing, in total, from 4 to 18 carbon atoms. Examples of such acyclic carboxylic acids are 2-ethylhexanoic acid and 3,3,5-trimethylhexanoic acid. Industrially, such acids are commonly obtained from aldehydes, either by direct oxidation or by initial reduction to an alcohol and subsequent oxidation of the alcohol. The aldehydes are most commonly obtained by reaction between an olefin, carbon monoxide and hydrogen in the presence of a catalyst at high temperatures and pressures, in what is known as the "oxo" or "hydroformylation" reaction. The composition of the acids so produced depends primarily on the composition of the olefin, which commonly is a commercial mixture of close homologues and isomers. The oxo reaction normally produces both primary and secondary aldehydes and thus both primary and secondary acids are produced from each olefin present.

Accordingly, there are available industrially mixtures containing all of the different primary and secondary acids capable of being produced from various olefin mixtures. Examples of such acids are "Acid 810" produced by AKZO, which consists of a mixture of $C_8$, $C_9$ and $C_{10}$ acids of the type described, and "isononanoic acid", produced by Hoechst (Ruhrchemie), which is a mixture of $C_9$ acids with a major proportion of the primary acid, 3,3,5-trimethylhexanoic acid.

Several variations on this and related manufacturing processes are known, those known as the "aldol" or "aldox" processes being particularly useful for producing such acids as the secondary acid, 2-ethylhexanoic acid. Any such acids may be used and acids of this type are sometimes known as "oxo acids" or "iso acids".

The tertiary saturated acyclic carboxylic acid [which is component (b) of the composition of the invention] is preferably, for reasons of commercial availability, a mixture of isomeric and homologous tertiary acids. Such acids preferably have the formula

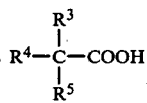

(in which $R^3$, $R^4$ and $R^5$ are the same or different and each represents an alkyl group, for example, a methyl, ethyl, n-propyl, isopropyl, n-butyl, isobutyl or t-butyl group). Such acids preferably contain from 6 to 20, and more preferably from 7 to 13, carbon atoms and thus $R^3$, $R^4$ and $R^5$ preferably contain a total of from 4 to 18 carbon atoms. Examples of such tertiary acids include 2-ethyl-2-methylhexanoic acid and 4-ethyl-2,2-dimethyloctanoic acid.

Industrially, such tertiary acids are commonly obtained by a two-stage reaction between olefins of the type $R^3R^4C=CH_2$ (in which $R^3$ and $R^4$ represent alkyl groups) with carbon monoxide and water at high pressure, in what is known as the "Koch" process. The composition of the acids produced by this process depends upon the composition of the olefin starting material, but the product will normally be a mixture of closely related homologues and isomers. Examples of mixtures of acids of this type are:

Versatic 10 (Shell), which is a mixture of isomeric tertiary acids of the above formula, such that $R^3+R^4+R^5$ together contain about 8 carbon atoms;

Versatic 911, where $R^3+R^4+R^5$ together contain from 7 to 9 carbon atoms, that is the entire molecule contains from 9 to 11 carbon atoms;

neudecanoic acid, produced by Exxon Chemical Company; and acid AGS-VA 340, supplied by AGS Chemicals and which is a mixture of saturated tertiary monocarboxylic acids, typically containing 92% by weight tertiary isomers of nonanoic acid, 3% by weight tertiary isomers of tridecanoic acid and that 1% each of tertiary isomers of $C_5$, $C_6$ and $C_7$ acids.

Tertiary acids of the type described above are sometimes referred to as "neo acids" or "trialkylacetic acids".

Commercially available primary, secondary and tertiary acids as described above are often a mixture of acids, whose composition may be very difficult to analyse. Indeed, it is even possible that some commercial primary and/or secondary acids may contain small quantities of tertiary acids and vice versa. For this reason, it is difficult to give a precise guide as to the ratio of primary and/or secondary acids to tertiary acids to use for best results. In general, we prefer that the ratio of primary and/or secondary acid(s) to tertiary acid(s) in the salts forming the composition of the invention should be from 90:10 to 10:90, more preferably from 75:25 to 25:75 and most preferably from 60:40 to 40:60, by weight. In practice, a convenient ratio is about 50:50 by weight of acids. These ratios are calculated on the basis of commercially available acid mixtures; should the pure acids be used (although, for reasons of economy, this is not preferred), the optimum ratios may be the same as those given above or they may vary slightly.

In order to be of value in preserving wood over a long period, a wood preservative must both be effective in preventing the growth of wood-destroying fungi and remain in the wood for a suitable length of time; thus, the preservative must not evaporate from the wood and must not be readily washed out by water. We have found that, when a mixture of the zinc or copper salts of primary and/or secondary acids with tertiary acids, as described above, is used, the fungicidal activity remaining after attempts have been made to evaporate and wash out the preservative composition is much greater than when either type of acid is used alone.

The composition of the present invention is preferably employed in the form of a solution in a suitable organic solvent. Such solvents include petroleum- and coal-derived solvents, such as white spirit, paraffin, gas oil, xylene or naphtha. However, the compositions may also be emulsified or dissolved in water with the aid of ammonia compounds or they may be formed directly in the material to be treated as a "two-bath" process.

The compositions of the invention may consist solely of the zinc or copper salts of primary and/or secondary acids and of tertiary acids or they may additionally include other known preservative, particularly wood preservative, materials, such as copper or zinc naphthenate, creosote or other tar oils, pentachlorophenol, tributyltin oxide, dichlofluanid, lindane or dieldrin. Resins, waxes and other water-repellent materials, dyes, pigments and tracers may also be incorporated into the composition.

Application of the compositions of the invention to wood for use as wood preservatives may be carried out by any of the known methods, for example by brushing, spraying, deluging, long or short immersion, double vacuum processes, double vacuum pressure processes or pressure processes, such as those known as Lowry, Bethel and Reuping processes. The concentration of zinc or copper salt in the composition may vary depending upon the method of application, although we generally prefer that the composition should contain from 0.5 to 4% by weight zinc or copper.

In addition to their use for preserving wood, the compositions of the invention may also be used for preventing biological degradation by fungi or insects in a variety of other degradable organic materials, for example fabrics, rope, cordage, nets, paper and boards and leather, in which case they may be applied by any of the known methods for treating such materials.

The invention is further illustrated by the following Examples, which are, however, not intended to limit the invention.

EXAMPLE 1

100 g of Versatic 10 (Shell) were mixed with 100 g of Acid 810 (AKZO) and 210 g of petroleum distillate. 64 g of powdered zinc oxide were added and the resulting mixture was stirred and heated to 90° C. until the zinc oxide dissolved, whereupon the temperature was increased to 140° C. to remove water. The product was a clear liquid containing 11.1% zinc. Further petroleum distillate was added to dilute the solution to a zinc content of 2.98% w/w. The resulting solution is hereafter referred to as "Solution 1".

For comparative purposes, similar solutions were prepared using either Versatic 10 or Acid 810 alone. "Solution 2" was prepared from 162 g of zinc oxide and 476 g of Acid 810 and was diluted to a zinc content of 2.99% w/w. "Solution 3" was prepared from 202 g of zinc oxide and 672 g of Versatic 10 and was diluted to a zinc content of 2.98% w/w.

Each of Solutions 1, 2 and 3 was diluted with petroleum spirit (boiling range 60°–80° C.) to prepare a series of dilute solutions containing 60, 45, 25, 15, 10 and 5% of Solutions 1, 2 or 3. Each of these dilute solutions was used to treat 12 blocks of Scots pine sapwood (*Pinus sylvestris*) of dimensions 5.0×2.5×1.5 cm, using the technique prescribed in British Standard 838:1961. Six of the blocks treated with each dilute solution were then subjected to a simulated ageing process, in which they were first immersed for one week at ambient temperature in water flowing at a rate of 2 liters per minute through a 225 liter container, after which they were placed around the circumference of a 1.2 meter diameter drum rotating 3 times per hour and passing, at one point in its rotation, close to a bank of three 2 kilowatt fan heaters blowing directly onto the blocks in such a way that the air temperature around the blocks near to the fan heaters was 66° C. and the temperature furthest away from the heaters was 32° C. The treatment in the rotating drum continued for 150 hours.

All twelve blocks from each treatment were then placed in contact with actively growing mycelium of *Coniophora cerebella* and incubated at 22° C. for 3 months following the technique described in British Standard No. 838:1961. At the end of this period, blocks were removed, cleaned, dried and weighed to determine the extent to which they had been attacked by the fungus, following the techniques of British Standard No. 838:1961.

From this we determined the highest initial treatment level at which the fungus was able to attack the wood (in terms of the amount of preservative in the wood for each of Solutions 1, 2 and 3) and the lowest initial treatment level which prevented attack. These results, referred to as "toxic limits", are shown in following Table 1.

TABLE 1

| Solution | Toxic limits (Kg/m³) | |
|---|---|---|
| | Unaged | Aged |
| 1 | 59–101 | 59–103 |
| 2 | 60–101 | 190–262 |
| 3 | 19–40 | 101–190 |

From these results, it can be seen that with Solution 1 (prepared from a mixture of acids according to the present invention) the level of initial treatment necessary to resist fungal attack after the wood has been subjected to a simulated ageing process is significantly lower than when either constituent acid is used alone and that the change in toxic limits caused by the ageing process is less, indicating greater resistance to ageing losses.

EXAMPLE 2

This Example follows the procedure of Example 1, except that a mixture of isononanoic acid (Hoechst)—an iso acid—and Versatic 10 (Shell)—a neo acid—was used.

129.7 g of isononanoic acid were mixed with 129.7 g of Versatic 10 in solution in petroleum distillate and the solution was reacted with 82 g of zinc oxide as described in Example 1 to produce an initial material containing 11.4% w/w zinc. Further petroleum distillate was added to this material to produce a Solution 4, which contained 3.02% w/w zinc.

This solution was compared, following the procedure described in Example 1, with Solution 3 and with a Solution 5 prepared from 81 g of zinc oxide and 245 g isononanoic acid and having a concentration adjusted to 3.02% w/w zinc.

The results obtained are shown in Table 2.

TABLE 2

| Solution | Toxic limits (Kg/m³) | |
|---|---|---|
| | Unaged | Aged |
| 4 | 18–40 | 39–60 |
| 5 | 59–100 | 98–190 |
| 3 | 19–40 | 101–190 |

It can be seen that the toxic limits for Solution 4, according to the present invention, after ageing are both lower and show less change than Solutions 5 and 3 containing the individual acids.

EXAMPLE 3

To a mixture of 28.44 g of 2-ethylhexanoic acid and 18.96 g of Acid AGS-VA 340 (acid value 343.7) were added 220 g of Shellsol E (a blend of aromatic solvents). 12.45 g of zinc oxide were then stirred in and the mixture was heated to 80°–90° C. and then allowed to react for 1 hour at 80°–90° C. The final product was a clear, yellow, stable product, which, on further dilution with 220 g of Shellsol E contained 2% by weight zinc. The molar ratio of zinc to total organic acids was 1:2. The weight ratio of 2-ethylhexanoic acid (a secondary acid) to Acid AGS-VA 340 (a tertiary acid) was 3:2.

EXAMPLE 4

To a mixture of 30.45 g of 2-ethylhexanoic acid and 45.67 of Versatic 10 acid were added 399 g of Shellsol E. 24.90 g of zinc oxide were then stirred in and the mixture was heated to 80°–90° C. and then allowed to react for 1 hour at this temperature. The final product was a clear, yellow, stable product containing 4% by weight zinc. The molar ratio of zinc to total organic acids in the product was 1.3:2 and the weight ratio of 2-ethylhexanoic acid (a secondary acid) to Versatic 10 acid (a tertiary acid) was 2:3.

EXAMPLES 5 to 10

Following substantially the same procedures as described in the preceding Examples, the following solutions, each containing approximately 3% by weight zinc (calculated as metal), were prepared:

EXAMPLE 5

Solution 6, containing zinc in the form of a 100% Versatic 10 acid salt, manufactured from:

| | |
|---|---|
| ZnO (Red Seal) | 112 g |
| Versatic 10 acid (acid value 321) | 370 g |
| Petroleum distillate | 418 g |
| Metal efficiency | 92.0 %. |

Diluted and analyzed at 2.99% by weight zinc.

EXAMPLE 6

Solution 7, containing zinc in the form of a salt of 75% by weight Versatic 10 acid and 25% by weight isononanoic acid. Manufactured from:

| | |
|---|---|
| ZnO | 75.7 g |
| Versatic 10 acid (acid value 321) | 180.6 g |
| Isononanoic acid (acid value 352) | 60.2 g |
| Petroleum distillate | 292.0 g |
| Metal efficiency | 97.9 %. |

Diluted and analyzed at 2.99% by weight zinc.

EXAMPLE 7

Solution 8, containing zinc salts of 50% by weight Versatic 10 acid and 50% by weight isononanoic acid. Manufactured from:

| | |
|---|---|
| ZnO | 75.7 g |
| Versatic 10 acid | 117.7 g |
| Isononanoic acid | 117.7 g |
| Petroleum distillate | 289.0 g |
| Metal efficiency | 96.0 %. |

Diluted and analyzed at 3.02% by weight zinc.

EXAMPLE 8

Solution 9, containing a zinc salt of 25% by weight Versatic 10 acid and 75% by weight isononanoic acid. Manufactured from:

| | |
|---|---|
| ZnO | 75.7 g |
| Versatic 10 acid | 57.5 g |
| Isononanoic acid | 172.5 g |
| Petroleum distillate | 294.0 g |
| Metal efficiency | 96.1 %. |

Diluted and analyzed at 2.98% by weight zinc.

EXAMPLE 9

Solution 10, containing the zinc salt of 100% isononanoic acid. Manufactured from:

| | |
|---|---|
| ZnO | 112.0 g |
| Isononanoic acid | 337.5 g |
| Petroleum distillate | 450.0 g. |
| Metal efficiency | 99.1 %. |

Diluted and analyzed at 2.97% zinc.

EXAMPLE 10

Solution 11, manufactured by mixing 951.5 g of Solution 1 with 1057.5 g of Solution 5.

MYCOLOGICAL TESTS

Each of these Solutions was separately diluted with white spirit to provide treating solutions containing 5, 10, 15, 20, 25, 30, 40, 50, 60, 70 or 80% by weight of the original Solution. 12 blocks (30×10×5 mm) of sapwood Scots Pine (*Pinus sylvestris L*) were treated with each of the diluted treating solutions by immersion in the treating solution whilst subjecting them to 380 mm Hg vacuum for 15 minutes, followed by 2 hours soaking at atmospheric pressure. The pickup in grams of preservative was recorded for each wood block and the mean preservative loading of the preservative solutions was calculated, as kilograms of preservative solution per cubic meter of wood.

After drying, half of each set of wood blocks was subjected to an artificial ageing regime, which consisted of immersing each set of 6 wood blocks in 200 ml of deionized water, the water being changed twice a day for 3 days (six times in all), allowing the blocks to dry for 30 hours and then putting them in a vacuum oven at 30° C. under a vacuum of 720 mm Hg for 72 hours.

Both aged and unaged test pieces were packed into polyethylene bags, heat-sealed and sterilized with 2.5 Mrad. of gamma radiation.

Cultures of the wood rotting fungus *Poria monticola* Murr. FPRL Strain 304D were inoculated onto 100 mm square petri dishes of agar containing 3% by weight malt extract and each dish containing 3 inert nylon grids. After the fungus had covered the agar, the sterilized test pieces were each placed on a nylon grid, 3 of the same preservative and concentration per petri dish. The dishes were then incubated at 22° C. and a relative humidity of 70%.

After incubation for 21 days, a visual assessment of fungal growth on each test piece was made, using the following ratings (Index of Condition):

0—No fungal growth in contact with the test piece.
1—Fungal growth on one or more sides but not the top of the test piece.
2—Fungal growth on one or more sides and covering not more than half of the top surface.
3—Fungal growth covering more than half of the top surface.

This Index of Condition (I/C) was averaged for each set of six identical blocks and graphs were drawn of mean I/C against loading (kg/m$^3$) of the zinc salt-containing preservative solutions. From these, the minimum preservative loading necessary to achieve an I/C value of 2 was determined and is recorded in the following Table 3.

TABLE 3

| Solution Preservative | Minimum loading Kg/m³ which gives an I/C rating of 2 | |
|---|---|---|
| | Unaged | Aged |
| 6 | 72 | 204 |
| 7 | 67 | 190 |
| 8 | 72 | 145 |
| 9 | 70 | 164 |
| 10 | 67 | 261 |
| 11 | 74 | 170 |

It can be seen that, although the fungicidal efficiencies of the solutions on the unaged wood blocks are of the same order, after ageing, the zinc soaps from mixtures of synthetic acids in accordance with the present invention (Solutions 7, 8 and 9) are appreciably more effective, as indicated by a lower initial treatment required to resist growth, than are the zinc soaps from single synthetic acids only (Solutions 6 and 10).

Solution 11, made by mixing Solutions 6 and 10 in approximately a 50:50 amount also shows the improved performance of mixtures over the single synthetic acid soaps.

EXAMPLES 11 to 16

Preparation of copper soaps

Caustic soda was dissolved in water to give a solution strength of approximately 30% by weight. This solution was then added to the chosen acid or mixture of acids, with continuous stirring. At this stage, the solution should have a slight excess of acid. In some cases, the sodium soap thus produced gave a very viscous solution and further water was added to produce a usable liquid, in each such case, however, the amount of added water was kept to a minimum. The petroleum distillate used as carrier solvent was then added in the amount specified in Table 4 and the temperature raised to 70°–80° C.

Meanwhile, copper sulphate pentahydrate was dissolved in water to give a solution strength of approximately 40% by weight copper sulphate pentahydrate. This solution was added to the sodium soap produced as described above and the temperature maintained at 70°–80° C. for 2–3 hours. The two phases were then allowed to separate and the aqueous layer run off from the bottom. This left a solvent solution of the copper soap with a copper content of approximately 5% by weight. This solution was analyzed and then adjusted to a copper content of around 2.7% by weight.

Details of the preparation and concentrations of the solutions are given in the following Table 4.

Mycological tests

Each of the Solutions prepared as described above was separately diluted with white spirit, to provide treating solutions each containing 5, 10, 15, 20, 25, 30, 35, 40, 50 or 70% by weight of the original Solution.

These treating solutions were then used to treat wood and the wooden samples were tested, precisely as described in Examples 5 to 10. After 21 days incubation, the sample wood blocks were assessed visually for fungal growth according to the 0–3 scale described in the previous Examples and an I/C was determined for each set of six wooden blocks. From these values, the minimum preservative loading necessary to achieve an I/C of 2 was determined graphically and the results are shown in Table 5.

TABLE 5

| | Preservative Solutions of salts | Minimum loading Kg/m³ which gave an I/C rating of 2 | |
|---|---|---|---|
| | | Unaged | Aged |
| 12. | Cu from 100% Versatic 10 acid | 52 | 82 |
| 13. | Cu from 75/25 Versatic 10/isononanoic acids | 96 | 75 |
| 14. | Cu from 50/50 Versatic 10/isononanoic acids | 65 | 86 |
| 15. | Cu from 25/75 Versatic 10/isononanoic acids | 82 | 99 |
| 16. | Cu from 100% isononanoic acid | 80 | 107 |
| 17. | Cu from 50/50 Versatic 10/isononanoic acids made by mixing 50/50 solutions 12 and 16 | 64 | 78 |

For aged test samples, the minimum loading of preservative necessary to achieve an I/C value of 2 is, as shown in the Table, 82 kg/cm³ for Solution 12 and 107 kg/cm³ for Solution 16. Based on these values, if the minimum loading value for mixtures were directly proportional to content of each of the acids, then the minimum loading for Solutions 13, 14 and 15 would be 88.25, 96.5 and 100.75 kg/cm³, respectively. In all cases, however, the actual values are lower. Similarly, the value to be expected for Solution 17 is 96.5 kg/cm³, but the value obtained is 78 kg/cm³. These results demonstrate improved efficiency of mixtures of acids over single synthetic acid soaps.

TABLE 4

| Ex. No. | Solution | Ratio Versatic 10:Isononanoic Acid | Versatic 10 Acid (g) | Isononanoic Acid (g) | Sodium hydroxide (g) | Petroleum Distillate (g) | CuSO₄ 5H₂O (g) | Final copper content % Cu w/w |
|---|---|---|---|---|---|---|---|---|
| 11 | 12 | 1:0 | 350 | 0 | 80 | 714 | 224 | 2.70 |
| 12 | 13 | 3:1 | 224.5 | 81.5 | 80 | 738 | 224 | 2.75 |
| 13 | 14 | 1:1 | 159.3 | 159.3 | 80 | 745 | 224 | 2.69 |
| 14 | 15 | 1:3 | 77.9 | 233.6 | 80 | 752 | 224 | 2.71 |
| 15 | 16 | 0:1 | 0 | 318 | 80 | 746 | 224 | 2.65 |
| 16 | 17 | 1:1 | Solution 12: 770 gms + Solution 16: 860 gms | | | | | 2.67 |

We claim:
1. A fungicidal composition comprising a mixture of:
    (a) a zinc salt of isononanoic acid and

(b) a zinc salt of a mixture of tertiary saturated acyclic carboxylic acids which acids have the formula

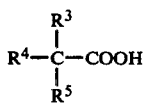

wherein $R^3$, $R^4$ and $R^5$ represent an alkyl group which together contain about 8 carbon atoms, the weight ratio of zinc salt of isononanoic to zinc salt of a said mixture of tertiary saturated acyclic carboxylic acids being 75:25 to 25:75.

2. A method of preserving wood which comprises impregnating said wood with a fungicidally effective amount of a solution of a composition according to claim 1.

* * * * *